US010285637B1

(12) United States Patent
Hnat et al.

(10) Patent No.: US 10,285,637 B1
(45) Date of Patent: May 14, 2019

(54) APPARATUS FOR SENSING STRAIN ON A SPINAL FUSION ROD

(71) Applicant: University of Louisville Research Foundation, Inc., Louisville, KY (US)

(72) Inventors: William P. Hnat, Floyds Knobs, IN (US); Michael J. Voor, Louisville, KY (US); Robert Louis Burden, Jr., Louisville, KY (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 367 days.

(21) Appl. No.: 14/937,300

(22) Filed: Nov. 10, 2015

Related U.S. Application Data

(60) Provisional application No. 62/077,543, filed on Nov. 10, 2014.

(51) Int. Cl.
*A61B 5/00* (2006.01)
*A61B 17/68* (2006.01)
*A61B 17/70* (2006.01)

(52) U.S. Cl.
CPC .......... *A61B 5/4566* (2013.01); *A61B 17/685* (2013.01); *A61B 17/7002* (2013.01); *A61B 17/7041* (2013.01); *A61B 2562/0261* (2013.01)

(58) Field of Classification Search
CPC ............ A61B 17/7002; A61B 17/7047; A61B 5/4566; A61B 17/685; A61B 2562/0261; A61B 17/7041; G01L 1/22; G01L 1/2206
USPC ..................................... 73/862.633
See application file for complete search history.

(56) References Cited

U.S. PATENT DOCUMENTS

| 3,411,348 | A | * | 11/1968 | Schultheis, Jr. | ...... G01L 1/2206 73/775 |
| 4,653,481 | A | * | 3/1987 | Howland | ........... A61B 17/7001 606/261 |
| 5,179,942 | A | | 1/1993 | Drulias et al. | |
| 5,709,685 | A | | 1/1998 | Dombrowski et al. | |
| 6,083,248 | A | | 7/2000 | Thompson | |
| 6,123,706 | A | * | 9/2000 | Lange | ................ A61B 17/7037 606/264 |
| 6,341,504 | B1 | | 1/2002 | Istook | |
| 7,302,858 | B2 | * | 12/2007 | Walsh | .................... A61B 5/103 73/780 |
| 7,357,037 | B2 | * | 4/2008 | Hnat | ........................ G01L 1/22 73/795 |
| 7,632,216 | B2 | | 12/2009 | Rahman et al. | |

(Continued)

FOREIGN PATENT DOCUMENTS

WO    WO 2013066946 A1 *  5/2013 ......... A61B 17/7002

*Primary Examiner* — David J. McCrosky
(74) *Attorney, Agent, or Firm* — Robert H. Eichenberger; Brantley C. Shumaker

(57) ABSTRACT

Systems, methods, and apparatus are described herein for obtaining medical diagnostic measurements from implanted sensors. In various embodiments, an apparatus may include two or more clamps to be rigidly clamped to the spinal fusion rod at a distance from one another, and a strain-sensing system that is removably mountable to the two or more clamps to span the distance. The strain-sensing system may include one or more strain-sensing elements. In various embodiments, the two or more clamps may be configured to transfer strain detected in the spinal fusion rod to the one or more strain-sensing elements of the strain-sensing system.

5 Claims, 4 Drawing Sheets

(56) References Cited

U.S. PATENT DOCUMENTS

| | | |
|---|---|---|
| 8,073,548 B2 | 12/2011 | Colvin, Jr. et al. |
| 2009/0275867 A1 | 11/2009 | Santos-Munne et al. |
| 2009/0299411 A1* | 12/2009 | Laskowitz ......... A61B 17/7008 606/246 |
| 2011/0125063 A1 | 5/2011 | Shalon et al. |
| 2011/0195666 A1 | 8/2011 | Forsell |
| 2012/0071793 A1 | 3/2012 | Gal |
| 2012/0123232 A1 | 5/2012 | Najarian et al. |
| 2012/0184826 A1 | 7/2012 | Keenan et al. |
| 2013/0079693 A1 | 3/2013 | Ranky et al. |
| 2014/0046403 A1 | 2/2014 | Aghassian |
| 2014/0062717 A1 | 3/2014 | Mudumbai et al. |

* cited by examiner

APPARATUS FOR SENSING STRAIN ON A SPINAL FUSION ROD

CROSS REFERENCE TO RELATED APPLICATION

This application claims priority to U.S. Provisional Patent Application Ser. No. 62/077,543, entitled "APPARATUS FOR SENSING STRAIN ON A SPINAL FUSION ROD," filed Nov. 10, 2014, the entirety of which is incorporated herein by reference.

BACKGROUND

Implanted sensors may measure, and make available to other devices using wireless technology, various medical diagnostic measurements such as strain readings, e.g., from body segments or joints in between. Often such measurements are obtained while visiting a doctor's office. The doctor may bring a device with a wireless reader (e.g., NFC, RFID, BlueTooth, etc.) into wireless range of one or more implanted sensors, e.g., in the patient's back, to wirelessly obtain medical diagnostic data from those sensors.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of embodiments of the invention.

DETAILED DESCRIPTION

Figure 1:
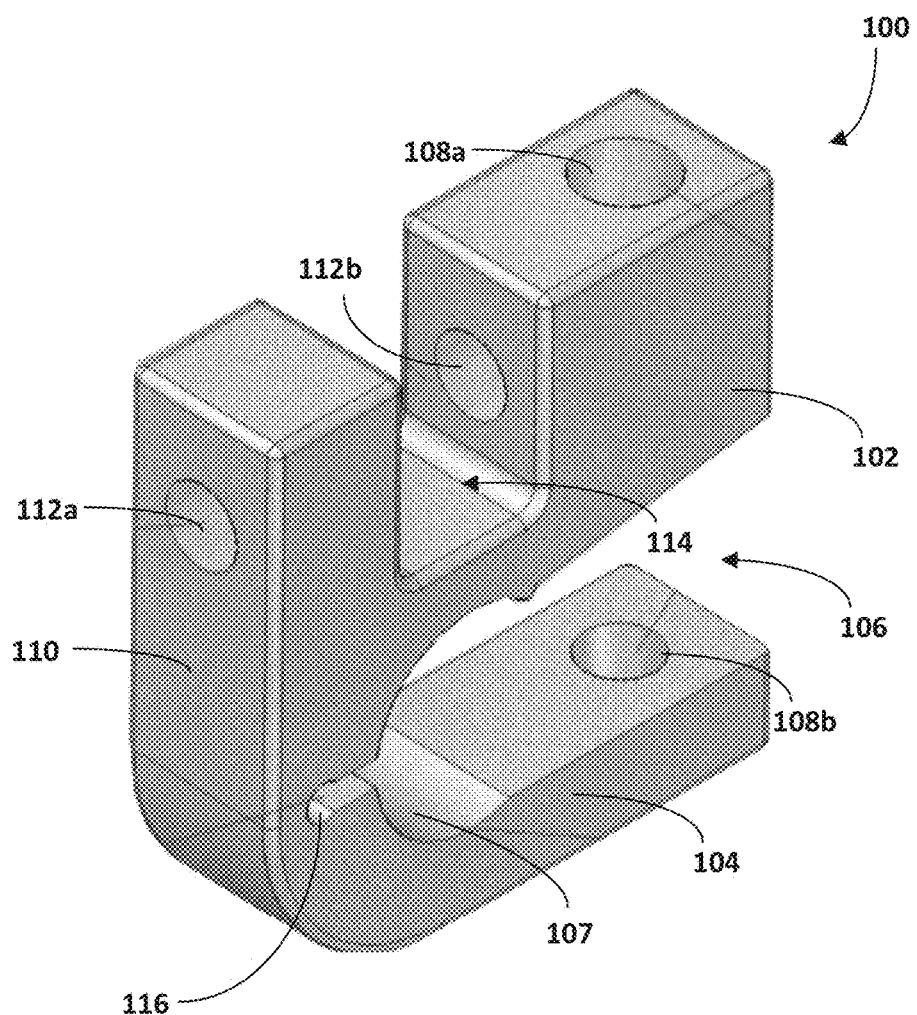
FIG. 1 is a perspective view of a first clamp, in accordance with various embodiments.
Figure 2:
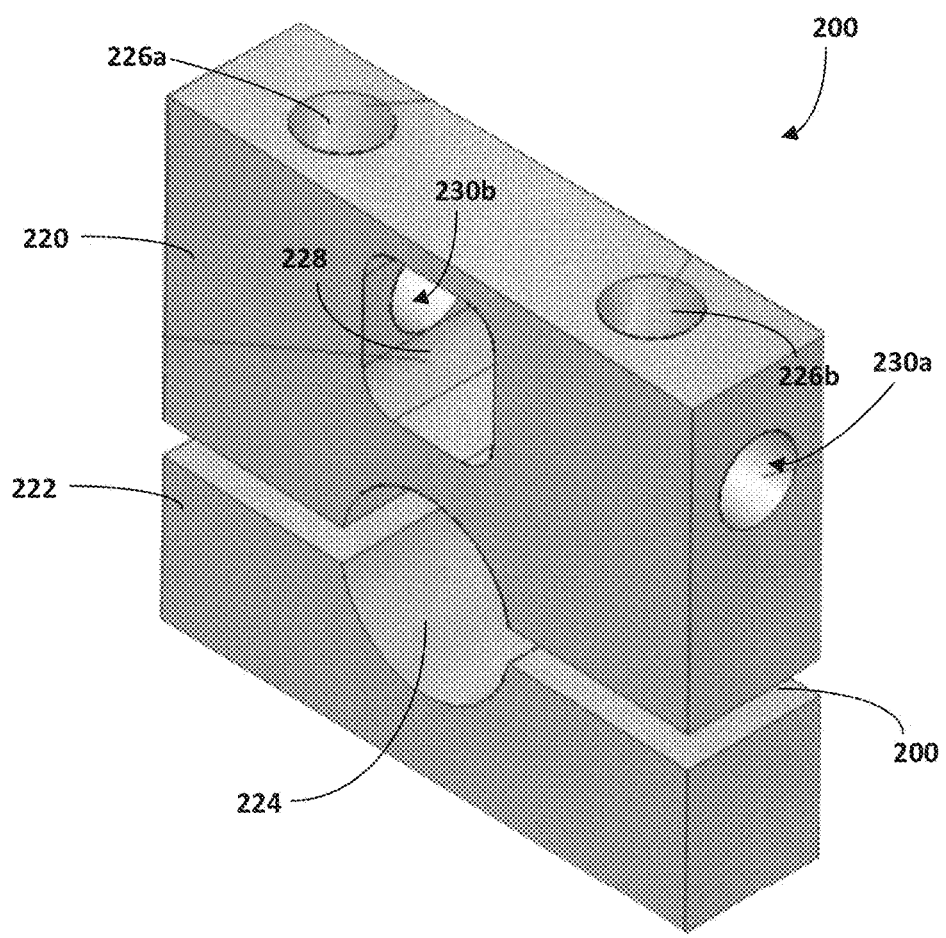
FIG. 2 is a perspective view of a second clamp, in accordance with various embodiments.
Figure 3:
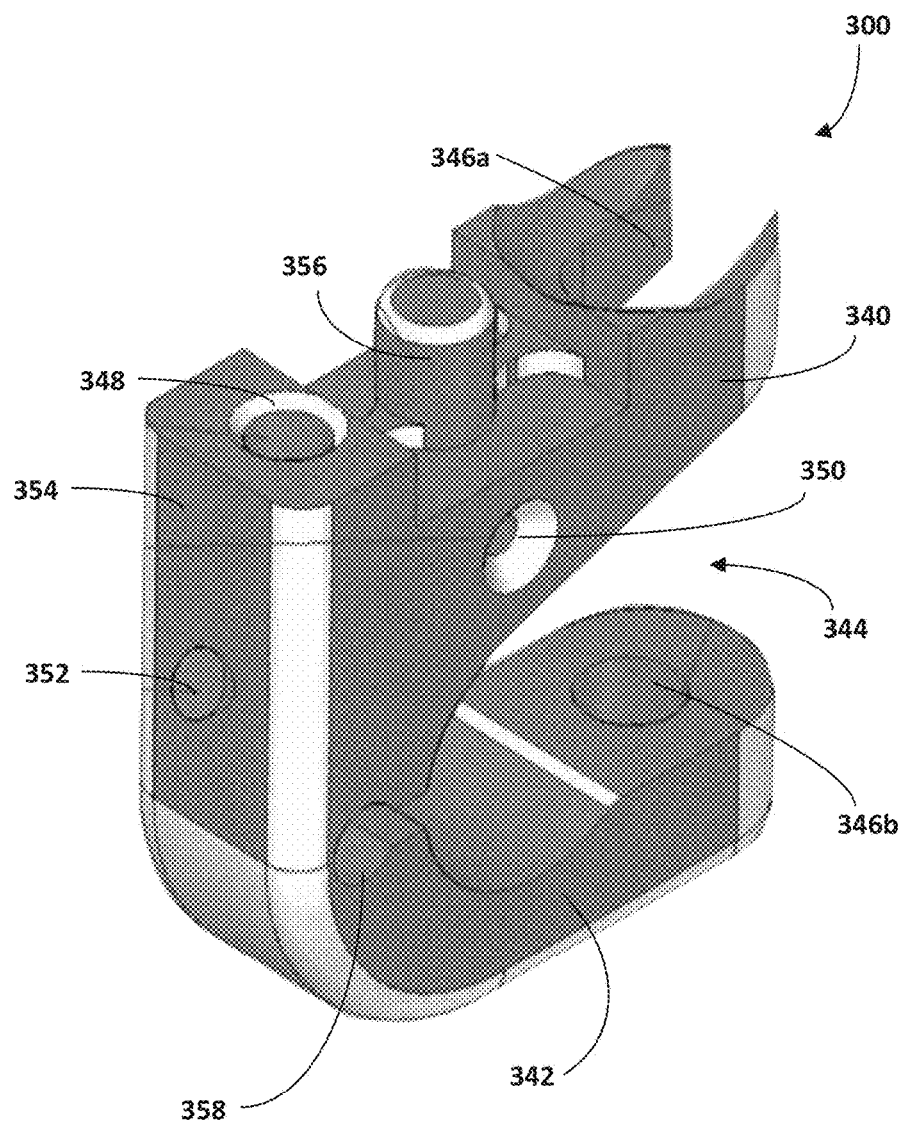
FIG. 3 is a perspective view of a third clamp, in accordance with various embodiments.

A strain-sensing system may be employed to measure and/or monitor strain on a straight or curved spinal fusion rod that is implanted in a patient. Strain-sensing systems may be secured to a spinal fusion rod using various clamping mechanisms. Three examples of clamps that may be used to secure a strain-sensing system to a spinal fusion rod are depicted in FIGS. 1-3. In each of these examples, the clamps may be configured to be rigidly secured to the spinal fusion rod at a distance from each other, while also being rotatable relative to each other to accommodate curved spinal fusion rods. The clamps may facilitate attachment of one or more sensing elements to measure strain on the spinal fusion rod. In some embodiments, the clamps may be configured to transfer strain imparted on or by the spinal fusion rod to one or more sensing elements of the strain-sensing system. It may be beneficial (though not required) for the clamps to be relatively small, as well as easy to install on an existing spinal fusion rod already implanted in a patient.

A first embodiment of a clamp 100 is depicted in FIG. 1. Clamp 100 may include a first portion 102 and a second portion 104. In between first portion 102 and second portion 104 may be a spinal fusion rod receiving area 106. Spinal fusion rod receiving area 106 may have a rounded portion 107 shaped to accommodate a spinal fusion rod (not depicted). Clamping apertures 108a and 108b may be located on first and second portions 102 and 104, respectively, and may be shaped to receive a screw or other fastening mechanism that may be used to move first and second portions 102 and 104 closer together, e.g., when a spinal fusion rod is inside of spinal fusion rod receiving area 106.

A spine 110 of clamp 100 may include strain-sensing system accommodation apertures 112a and 112b. In various embodiments, a screw, pin or other similar device may be inserted through strain-sensing system accommodation apertures 112a and 112b. This may hold one or more sensing elements (not depicted) of a strain-sensing system (also not depicted) in place, as well as transfer a force imparted on clamp 100 (e.g., by strain in a spinal fusion rod) to the strain-sensing system while clamp 100 remains rigidly secured to the spinal fusion rod.

In some embodiments, a channel 114 may be formed in first portion 102. Channel 114 may be wide enough to accommodate a variety of sensing elements and/or strain-sensing systems. In some embodiments, channel 114 is wide enough to facilitate encapsulation of a strain-sensing system, e.g., to protect one or more sensing elements. In some embodiments, the pins or screws that are inserted through strain-sensing system accommodation apertures 112a and 112b may suspend the strain-sensing system (or one or more sensing elements thereof) within channel 114.

In various embodiments, a notch 116 may be formed within spinal fusion rod receiving area 106. Notch 116 may allow for at least some flexibility between first portion 102 and second portion 104 when they are being clamped onto a spinal fusion rod, helping to avoid failure of clamp 100. In some embodiments, notch 116 may include a rounded terminal portion that may allow for more flexibility than if the rounded terminal portion were not present.

A second embodiment of a clamp 200 is depicted in FIG. 2. Clamp 200 may include a first portion 220 and a second portion 222. Between first portion 220 and second portion 222 may be an aperture 224 shaped to receive a spinal fusion rod (not depicted). Clamping apertures 226a and 226b may be shaped to receive a fastening mechanism (not depicted) such as a screw or pin, which may be inserted and/or operated through clamping apertures 226a and 226b into corresponding clamping apertures (not visible in FIG. 2) in a top surface of second portion 222. In this manner, clamp first portion 220 and second portion 222 may be clamped together rigidly onto a spinal fusion rod.

An opening 228 may be formed in first portion 220 to accommodate one or more sensing elements (not depicted) of a strain-sensing system (also not depicted). In some embodiments, the opening 228 may be configured to reduce or prevent outside interference with the strain-sensing system, and may be shaped to accommodate an encapsulated stain-sensing system and/or sensing elements thereof. Side apertures 230a and 230b may be configured to receive another fastening mechanism (not depicted) such as a pin or screw. Insertion of the pin or screw through side apertures 230a and 230b may facilitate suspension of the strain-sensing system or one or more sensing elements thereof within opening 228. In some embodiments, this also may allow force to be applied to clamp 200 along the same axis as the pins that are inserted through side apertures 230a and 230b.

A third embodiment of a clamp 300 is depicted in FIG. 3. Once again, a first portion 340 and a second portion 342 may define a spinal fusion rod receiving area 344 in between them. First portion 340 and second portion 342 may be clamped together by inserting a fastening mechanism (not depicted) such as a pin or screw through clamping apertures 346a and 346b. In this example, first clamping aperture 346a may not be entirely closed, but instead may be partially open and may define a channel aligned with second clamping aperture 346b. Having first clamping aperture 346a partially open may allow the fastener to be more easily inserted into and/or aligned with the channel between first clamping aperture 346a and second clamping aperture 346b during surgery.

A top aperture 348 may be configured to receive a screw or pin associated with a strain-sensing system or one or more sensing elements thereof. The strain-sensing system may in some embodiments be contained in a housing that is removably attachable to clamp 300 at top aperture 348. A side aperture 350 may be formed on a side surface of first portion 340. Side aperture 350 may provide an interface for a tool to be inserted to apply pre-tension to one or more sensing elements of a strain-sensing system, e.g., by separating clamp 300 from another, similar clamp (not depicted) with a selected force.

In some embodiments, a support member 352 may be disposed on a spine 354 of clamp 300 to assist in supporting a strain-sensing system on clamp 300. In some embodiments, a peg 356 may be disposed on first portion 340 of clamp 300. Peg 356 may be used, for instance, for mounting one or more sensing elements of a strain-sensing system. Peg 356 may in some instances transfer force applied to clamp 300, e.g., by a spinal fusion rod, into one or more sensing elements. Similar to clamp 100, clamp 300 may include in spinal fusion rod receiving area 344 a notch 358, which may permit additional flexibility between first portion 340 and second portion 342.

Figure 4:
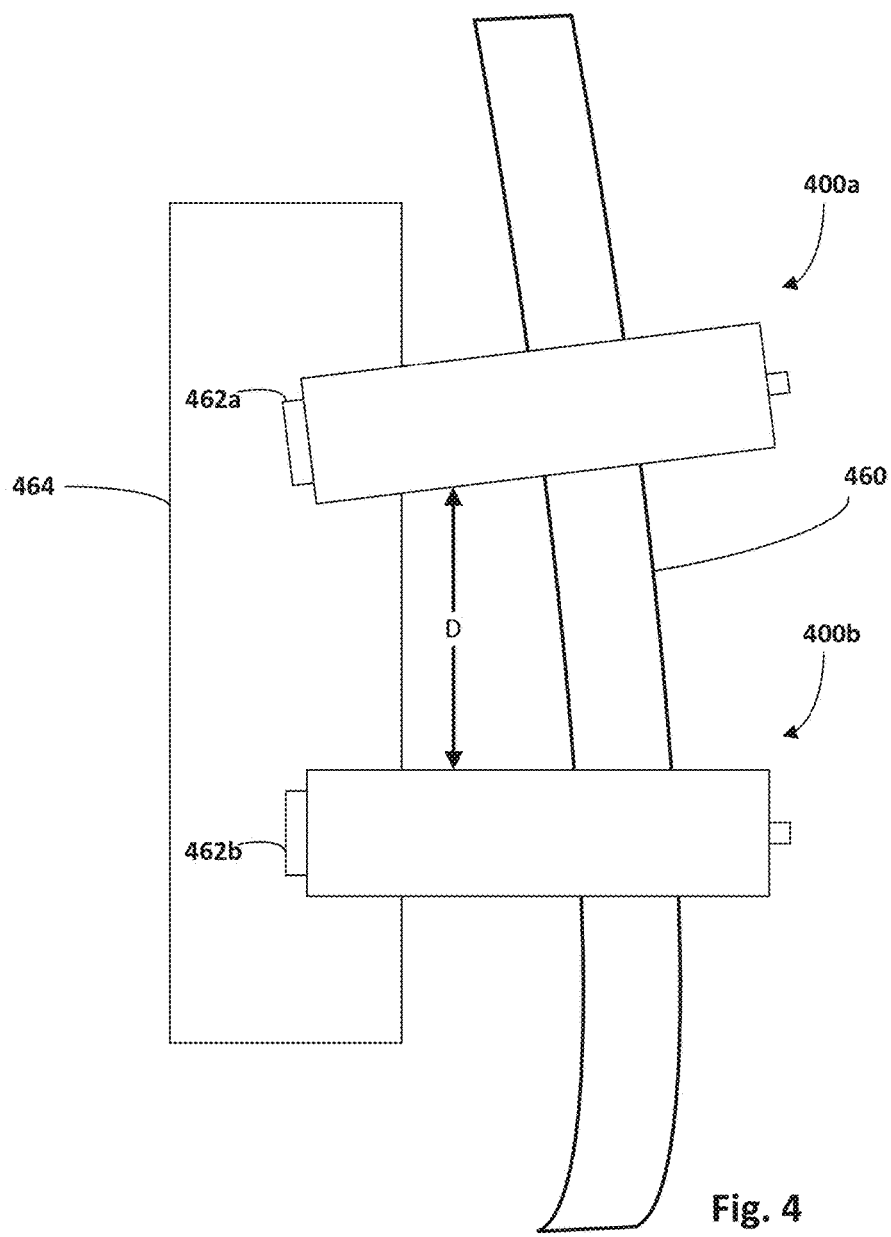
FIG. 4 schematically depicts an example strain-sensing system mounted on clamps configured with selected aspects of the present disclosure.

As mentioned above, a strain-sensing system may be mounted to one or more clamps (e.g., 100, 200, 300), and may be configured to receive force transferred by the clamps from a spinal fusion rod, e.g., caused by displacement of one or more clamps along the spinal fusion rod. FIG. 4 schematically depicts an example in which two clamps 400a and 400b, both configured with selected aspects of the present disclosure, have been secured to a curved spinal fusion rod 460 using fastening screws 462a and 462b, respectively. Because spinal fusion rod 460 is curved, clamps 400a and 400b are at slight angles to each other. If spinal fusion rod 460 were straight, which is also contemplated herein, clamps 400a and 400b would be at less (or no) angle relative to each other.

A strain-sensing system 464 may be mounted to clamps 400a and 400b to span a distance D between them, and may include one or more sensing elements that are not depicted. In some instances, strain-sensing system 464 may be referred to as a "bridge" because it spans clamps 400a and 400b. Clamps 400a and 400b may be configured to, by virtue of their rigid attachment to spinal fusion rod 460, transmit any displacement of the surface of spinal fusion rod 460 to one or more sensing elements of strain-sensing system 464. Various gauges may be employed in strain-sensing system 464 to measure strain on a surface of spinal fusion rod 460. This measured strain may be indicative of strain, displacement, and/or force imparted on spinal fusion rod 460. In some embodiments, strain-sensing system 464 may be shaped or otherwise designed to dampen the strain sensed at spinal fusion rod 460. In other embodiments, strain-sensing system 464 may be shaped or otherwise designed to amplify the strain sensed at spinal fusion rod 460. In some embodiments, structure of strain-sensing system 464 may include a frangible portion that may act as a predictable point of failure should too much force be imparted. This may prevent exposure of electronic components to a biological environment (or vice versa).

In some embodiments, a gauge (not depicted) such as a strain gauge may be mounted on a surface of strain-sensing system 464, such that alteration of a shape of strain-sensing system 464 may likewise alter the gauge. Thus, changes in geometry of strain-sensing system 464 and how it is mounted to clamps 400a and 400b may increase or decrease a percentage of the actual strain exhibited at spinal fusion rod 460 that is transferred to strain-sensing system 464. For example, a transfer of force from spinal fusion rod 460 to a strain gauge (or "sensor") of strain-sensing system 464 may be directly proportional to any change in a distance between axes of mounting pins (not depicted) that are used to mount strain-sensing system 464 to clamps 400a and 400b, a height of a center of these mounting pins from a center of spinal fusion rod 460, and/or a thickness of strain-sensing system 464. Conversely, a transfer of force from spinal fusion rod 460 to a strain gauge of strain-sensing system 464 may be inversely proportional to any change in a span length of strain-sensing system 464 across clamps 400a and 400b (e.g., a change in a span length such as that depicted by distance D), and/or an offset of strain-sensing system 464 from a center of axes of mounting pins (not depicted) that are used to mount strain-sensing system 464 to clamps 400a and 400b.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification, unless clearly indicated to the contrary, should be understood to mean "at least one."

The phrase "and/or," as used herein in the specification, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

As used herein in the specification, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. An apparatus for sensing strain on a spinal fusion rod, comprising:
    two or more clamps to be rigidly clamped to the spinal fusion rod at a distance from one another, wherein each of the two or more clamps is formed as a unitary and continuous component that includes a spine and first and second portions that extend from the spine parallel to one another to define a spinal fusion rod receiving area therebetween, wherein the spine includes a notch to facilitate flexibility between the first and second portions such that they are movable toward each other to pinch the spinal fusion rod; and
    a strain-sensing system that is removably mountable to the two or more clamps to span the distance, the strain-sensing system including one or more strain-sensing elements, and wherein the two or more clamps define a channel in which the strain-sensing system is suspended;
    wherein the two or more clamps are configured to transfer strain detected in the straight or curved spinal fusion rod to the one or more strain-sensing elements of the strain-sensing system.

2. The apparatus according to claim 1, wherein the one or more strain-sensing elements comprise one or more strain gauges.

3. The apparatus of claim 1, wherein the notch includes a rounded terminal portion.

4. The apparatus of claim 1, wherein the first and second portions include respective clamping apertures that are aligned with each other to receive a fastening mechanism.

5. The apparatus of claim 4, wherein at least one of the clamping apertures is at least partially open to receive the fastening mechanism from a lateral direction.

\* \* \* \* \*